US012708080B2

(12) United States Patent
Zhang et al.

(10) Patent No.: US 12,708,080 B2
(45) Date of Patent: Aug. 18, 2026

(54) METHOD FOR MAGNETIC TRANSFECTION OF MAIZE POLLEN

(71) Applicant: Beijing Academy of Agriculture and Forestry Sciences, Beijing (CN)

(72) Inventors: Zhongbao Zhang, Beijing (CN); Zhongyi Wu, Beijing (CN); Zuoping Wang, Beijing (CN)

( * ) Notice: Subject to any disclaimer, the term of this patent is extended or adjusted under 35 U.S.C. 154(b) by 315 days.

(21) Appl. No.: 18/203,113

(22) Filed: May 30, 2023

(65) Prior Publication Data

US 2023/0301256 A1 Sep. 28, 2023

Related U.S. Application Data

(63) Continuation of application No. PCT/CN2022/125244, filed on Oct. 14, 2022.

(30) Foreign Application Priority Data

Nov. 26, 2021 (CN) ........................ 202111418727.8

(51) Int. Cl.
*B82Y 5/00* (2011.01)
*A01H 1/02* (2006.01)

(52) U.S. Cl.
CPC ................ *A01H 1/027* (2021.01); *B82Y 5/00* (2013.01)

(58) Field of Classification Search
None
See application file for complete search history.

(56) References Cited

U.S. PATENT DOCUMENTS

| | | | |
|---|---|---|---|
| 2003/0145346 | A1 | 7/2003 | Hood et al. |
| 2020/0354732 | A1 | 11/2020 | Issa et al. |

FOREIGN PATENT DOCUMENTS

| | | | |
|---|---|---|---|
| CN | 110331167 | A | 10/2019 |
| CN | 114085866 | A | 2/2022 |

OTHER PUBLICATIONS

Zhang et al., Novel Pollen Magnetofection System forTransformation of Cotton Plant with Magnetic Nanoparticles as Gene Carriers, 2018, Methods in Molecular Biology; Transgenic Cotton, vol. 1902, pp. 47-54 (Year: 2018).*

Yang et al., Expression of Foreign Genes Demonstrates the Effectiveness of Pollen-Mediated Transformation in *Zea mays*, 2017, Frontiers in Plant Science, vol. 8(383), pp. 1-10 (Year: 2017).*

Wang et al., Efficient and Genotype Independent Maize pollen Transfection Mediated by Magnetic Nanoparticles, 2020, Research Square, Pre-print (Year: 2020).*

Hartman, R., Exploring maize pollen with microscopy: confocal, fluorescence and time-lapse imaging, 2020, Honors Baccalaureate Thesis, Oregon State University (Year: 2020).*

Chinese Intellectual Property Office (ISR/CN), "International Search Report for PCT/CN2022/125244", China, Jan. 18, 2023.

Yanjing et al., Preliminary Analysis on Transgenic Technology of Pollen-Mediated by Magnetic Nanoparticles in Tree Peony, 2020.

Xiang Zhao et al., Pollen magnetofection for genetic modification with magnetic nanoparticles as gene carriers, Nature Plants, 2017.

* cited by examiner

*Primary Examiner* — Amjad Abraham
*Assistant Examiner* — Christina L Meadows

(57) ABSTRACT

The present invention discloses an improved method for magnetic transfection of maize pollen, including: (1) preparing plasmid DNA for transfection; (2) binding MNP nanomagnetic beads to the plasmid DNA at room temperature to form MNP-DNA complex; (3) collecting fresh pollen from maize at full flowering and bringing it rapidly back indoors under ice box storage conditions insulated from water; (4) mixing a maize pollen transformation solution with sieved maize pollen and being subjected to aperture-opening pre-treatment at low temperature; (5) adding the MNP-DNA complex to aperture-opening pre-treatment solution, mixing gently and placing on a low temperature pre-cooled magnetic plate for transfection; (6) after transfection, taking the pollen suspension to field in ice box and pollinating directly on ears of maize. The present invention directly uses maize grown in the field for transformation, requires only conventional refrigeration equipment, is simple and inexpensive to operate and is applicable to all maize varieties.

6 Claims, 18 Drawing Sheets

METHOD FOR MAGNETIC TRANSFECTION OF MAIZE POLLEN

CROSS-REFERENCE TO RELATED APPLICATION

This application is a continuation application of International Patent Application No. PCT/CN2022/125244, filed on Oct. 14, 2022, which itself claims priority to and benefit of Chinese Patent Application No. 202111418727.8 filed on Nov. 26, 2021 in the State Intellectual Property Office of P. R. China. The disclosure of each of the above applications is incorporated herein by reference in its entirety.

FIELD OF THE INVENTION

The present invention belongs to the field of plant genetic engineering and specifically relates to an improved method for magnetic transfection of maize pollen that both maintains pollen viability and increases transformation efficiency.

BACKGROUND OF THE INVENTION

Maize is a crop that is widely grown globally to meet the growing demand for food, feed and fuel. Despite significant improvements in maize yield and quality through traditional breeding over the last two centuries, it still faces serious challenges from a variety of biotic and abiotic stresses. To meet these challenges, transgenic maize has been developed to introduce desired traits such as insect and herbicide resistance, drought tolerance, cold tolerance and improved nutritional quality. Efficient genetic transformation is key to the development of transgenic maize. Since the first successful protoplast-based transformation of maize by electroporation in 1988, scientists have developed a variety of methods to obtain transgenic maize plants, such as gene gun, Agrobacterium-mediated, PEG-mediated, liposome-mediated, carbon-mediated, and microinjection methods. However, these methods rely mainly on tissue culture systems, which are costly, labor-intensive and time-consuming, and are particularly dependent on the genotype. Only a few maize varieties have relatively high genetic transformation efficiency, such as Hi II, B104 and A188. Most good maize inbred lines have technical barriers that limit their commercial application, particularly in the development of advanced breeding techniques such as precision genome editing directly in good crop germplasm. It is therefore important to establish an efficient gene delivery system in all maize varieties that allows for direct and precise molecular improvement.

SUMMARY OF THE INVENTION

An object of the present invention is to develop an improved method for magnetic transfection of maize pollen that both maintains pollen viability and increases transformation efficiency, which directly uses maize grown in the field for transformation, requires only conventional refrigeration equipment, is simple and inexpensive to operate and is applicable to all maize varieties. The object of the present invention is achieved by the following technical solutions:

An improved method for magnetic transfection of maize pollen, in which maize pollen is kept at low temperature throughout the process from pollen collection to pollination, to maximize the viability of maize pollen; and the low temperature pretreatment of the transformation solution opens the maize pollen apertures originally with operculum, which is more conducive to the introduction of exogenous DNA. The target gene is introduced into maize pollen, allowing transient expression of the target gene in the pollen. After pollination, more transformed seeds can be obtained for subsequent screening and identification.

An improved method for magnetic transfection of maize pollen, comprising the following steps of:

(1) preparing plasmid DNA for transfection;

(2) binding MNP nanomagnetic beads to the plasmid DNA at room temperature to form MNP-DNA complex;

(3) collecting fresh pollen from maize at full flowering and bringing it rapidly back indoors under ice box storage conditions insulated from water;

(4) mixing a maize pollen transformation solution with sieved maize pollen and being subjected to aperture-opening pre-treatment at low temperature;

(5) adding the MNP-DNA complex obtained in step (2) to aperture-opening pre-treatment solution of step (4), mixing gently and placing on a low temperature pre-cooled magnetic plate for transfection;

(6) after transfection, taking the pollen suspension to field in ice box and pollinating directly on ears of maize;

wherein, in step (4) and step (5), the low temperature is 6 to 10° C.

According to the improved method for magnetic transfection of maize pollen, wherein: the low temperature is 8° C.

According to the improved method for magnetic transfection of maize pollen, wherein: step (1) specifically comprises the following steps: high purity plasmid DNA for transfection was extracted in bulk, adjusted to a concentration of 1000±50 ng/μL with $ddH_2O$, dispensed in small tubes and stored frozen at −20° C. to avoid repeated freeze-thawing, and the plasmid DNA was taken out and thawed to room temperature prior to magnetic transfection.

According to the improved method for magnetic transfection of maize pollen, wherein: step (2) specifically comprises the following steps: based on the flowering status of maize inbred lines and plasmid transformation requirement, the transformation trials to be carried out on the day were estimated; the nanomagnetic beads MNP were allowed to stand at room temperature for 10 min, a 200 μL PCR tube with the transformation number written on the cap was added with 160 μL of $ddH_2O$, 7.5 μL of 1 μg/μL of magnetic nanobeads and 30 μL of 1 μg/μL of DNA, mixed by gentle aspiration and allowed to stand at room temperature for 20 min or more to obtain the MNP-DNA complex.

According to the improved method for magnetic transfection of maize pollen, wherein: step (3) specifically comprises the following steps: fresh pollen was collected in paper bags from maize inbred lines at flowering, and the powdered paper bags were taken in plastic self-sealing bags, sandwiched between ice packs and quickly brought back to the chamber in ice boxes for magnetic transfection.

According to the improved method for magnetic transfection of maize pollen, wherein: step (4) specifically comprises the following steps: the anthers were removed from the pollen obtained in step (3) using a 100 mesh sieve, approximately 2 g of the sieved pollen were weighed and transferred to a 15 mL round-bottom centrifuge tube with the transformation number marked on the wall, 8 mL of maize pollen transformation solution pre-cooled at 8° C. were added, covered tightly and mixed thoroughly upside down, and the tube was left horizontally for aperture-opening for 10 min in an 8° C. incubator, The content of each component in the maize pollen transformation solution was: sucrose 0.5 mol/L, $H_3BO_3$ 1 mmol/L, $KNO_3$ 1 mmol/L, Ca $(NO_3)_2$ 1 mmol/L, $MnSO_4 \cdot H_2O$ 1 mmol/L, $MgSO_4 \cdot 7H_2O$ 1 mmol/L, $GA_3$ 0.1 mmol/L.

According to the improved method for magnetic transfection of maize pollen, wherein: step (5) specifically comprises the following steps: the MNP-DNA obtained in step (2) was entirely added to the aperture-opening pre-treatment solution in step (4), total volume approximately 10 mL, gently inverted and mixed, placed on a MagnetoFACTOR-96 plate pre-cooled in an incubator at 8° C., and placed horizontally for transfection for 10 min, then gently inverted and mixed once, and again placed horizontally for transfection for 10 min, for a total of 20 min.

According to the improved method for magnetic transfection of maize pollen, wherein: step (6) specifically comprises the following steps: after magnetic transfection, the pollen centrifuge tube was clamped in a pre-cooled ice bag at 8° C. and quickly taken to the field in an ice box; the pollen was gently shaken upside down and pollinated on 10 ears of pre-bagged maize inbred lines that were spitting; a drop of pollen suspension was added to the maize filaments truncated to approximately 2 cm long with a de-tipped 1 mL tip, 1 mL/ear, and the pollen suspension was spread evenly with gloves, After pollinating the pollen of one plasmid, the pollen of the next plasmid was pollinated with a new glove, 20 days after the pollination, fruiting seeds were visible.

The improved method for magnetic transfection of maize pollen of the present invention differs from the prior art in that:

Firstly, the present invention has improved the method for magnetic transfection of maize pollen by magnetically transfecting maize pollen in a low temperature environment, which reduces the activity of degradative enzymes within the pollen and is more conducive to maintaining the viability status and integrity of the pollen. Secondly, the pollen is pretreated for 10 minutes at low temperature using transformation solution in order to induce opening of the operculum of pollen aperture, breaking the barrier of the cell wall and facilitating the entry of exogenous DNA through the pollen aperture by the magnetic transfection method into the pollen cells and improving the transformation efficiency. The transfection method is faster and can be completed in 0.5 to 1 hour from the collection of maize pollen to the completion of transfection and pollination, maximizing the viability of maize pollen, increasing the fertility of the pollinated ears and allowing more transformed seeds to be obtained for subsequent screening and identification. Thirdly, the method is simple and efficient, requiring only the provision of conventional refrigeration equipment and an established magnetic field to complete the transformation, eliminating the need for expensive instrumentation and allowing for large-scale maize transformation in the field and on site.

The improved method for magnetic transfection of maize pollen of the present invention is further described below in conjunction with the accompanying drawings.

BRIEF DESCRIPTION OF THE DRAWINGS

Additional objectives, functions, and advantages of the present invention will be set forth in the description of embodiments which follow, with reference to the accompanying drawings in which.

DETAILED DESCRIPTION OF THE INVENTION

An improved method for magnetic transfection of maize pollen:

Nanomagnetic beads (MNP, item no. 9006) and magnetic plates (item no. 9008-96) were purchased from Chemicell, Germany.

The maize inbred lines were 178, HZ178, Jing 92 and Zheng 58.

The specific maize pollen magnetic transfection process is shown in FIG. 1 to FIG. 5.

(1) High purity plasmid DNA for transfection was extracted in bulk, adjusted to a concentration of 1000±50 ng/μL with $ddH_2O$, dispensed in small tubes and stored frozen at −20° C. to avoid repeated freeze-thawing, and the plasmid DNA was taken out and thawed to room temperature prior to magnetic transfection.

(2) Based on the flowering status of maize inbred lines and plasmid transformation requirement, the transformation trials to be carried out on the day were estimated; the nanomagnetic beads MNP were allowed to stand at room temperature for 10 min, a 200 μL PCR tube with the transformation number written on the cap was added with 160 μL of $ddH_2O$, 7.5 μL of 1 μg/μL of magnetic nanobeads and 30 μL of 1 μg/μL of DNA, mixed by gentle aspiration and allowed to stand at room temperature for 20 min or more to obtain the MNP-DNA complex.

(3) Fresh pollen was collected in paper bags from maize inbred lines at flowering (FIG. 1), and the powdered paper bags were taken in plastic self-sealing bags, sandwiched between pre-cooled ice packs at 8° C. and quickly brought back to the chamber in ice boxes for magnetic transfection.

(4) The anthers were removed from the pollen obtained in step (3) using a 100 mesh sieve (FIG. 2), approximately 2 g of the sieved pollen were weighed and transferred to a 15 mL round-bottom centrifuge tube (marked with the transformation number on the wall), 8 mL of maize pollen transformation solution pre-cooled at 8° C. were added, covered tightly and mixed thoroughly upside down, and the tube was left horizontally for aperture-opening for 10 min in an 8° C. incubator. The content of each component in the maize pollen transformation solution was: sucrose 0.5 mol/L, $H_3BO_3$ 1 mmol/L, $KNO_3$ 1 mmol/L, $Ca(NO_3)_2$ 1 mmol/L, $MnSO_4 \cdot H_2O$ 1 mmol/L, $MgSO_4 \cdot 7H_2O$ 1 mmol/L, $GA_3$ 0.1 mmol/L.

Figure 1:
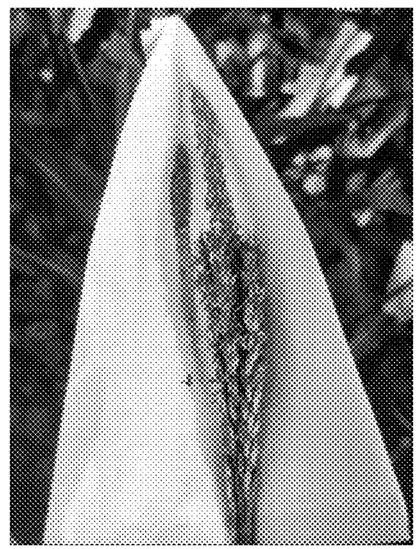
FIG. 1 shows a schematic diagram of collecting fresh maize pollen at full flowering in the method of the present invention.
Figure 2:
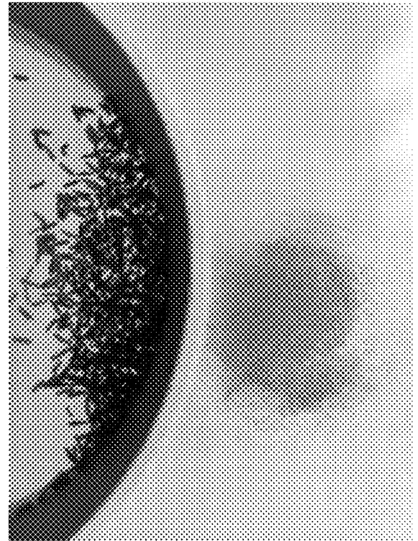
FIG. 2 shows a schematic diagram of screening out anthers in the method of the present invention.
Figure 3:
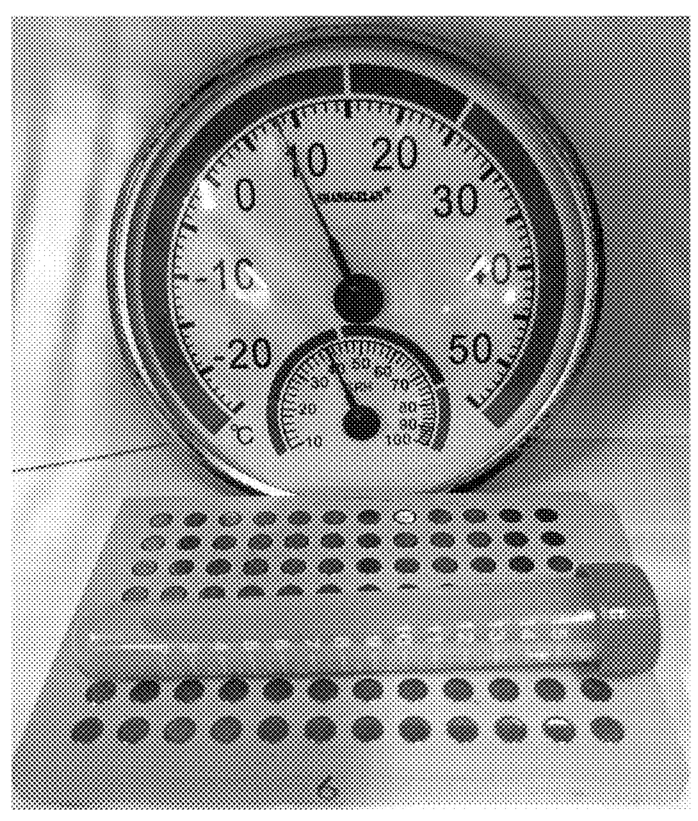
FIG. 3 shows a schematic diagram of low temperature magnetic transfection in the method of the present invention.

(5) The MNP-DNA obtained in step (2) was entirely added to the aperture-opening pre-treatment solution in step (4) (total volume approximately 10 mL), gently inverted and mixed, placed on a MagnetoFACTOR-96 plate (up to four 15 mL round-bottom centrifuge tubes per plate) pre-cooled in an incubator at 8° C., and placed horizontally for transfection for 10 min, then gently inverted and mixed once, and again placed horizontally for transfection for 10 min, for a total of 20 min (FIG. 3).

Figure 4:
FIG. 4 shows a schematic diagram of applying a pollen suspension to maize filaments in the method of the present invention.
Figure 5:
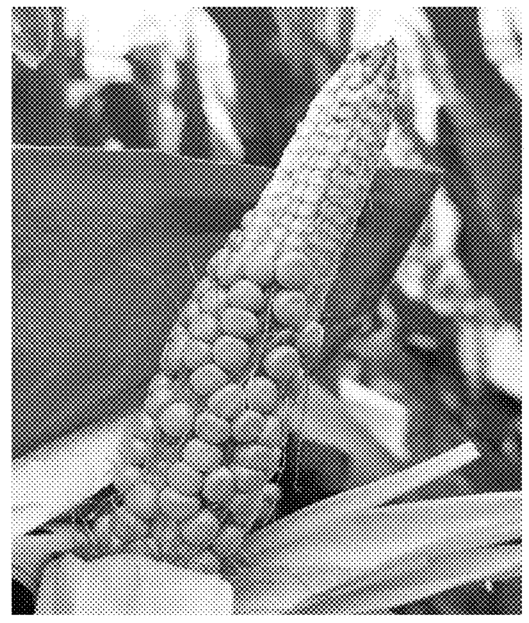
FIG. 5 shows a schematic diagram of setting of maize 20 days after pollination with magnetically transfected pollen in the method of the present invention.
Figure 6:
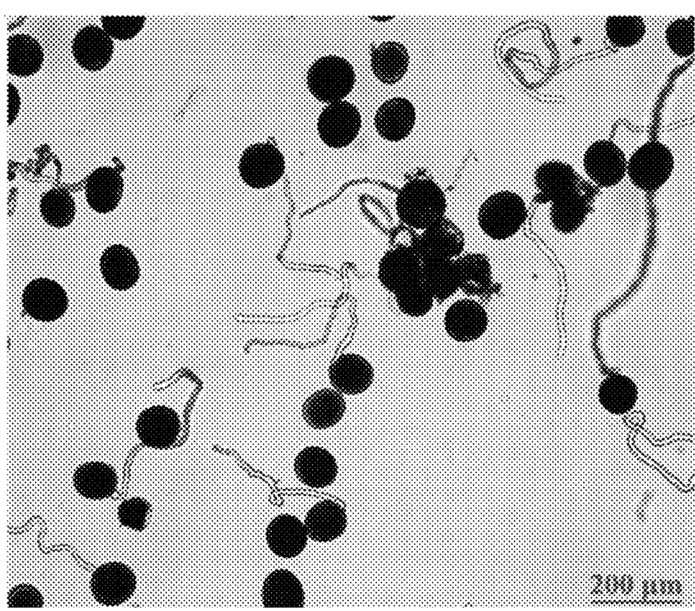
FIG. 6 shows direct germination of fresh maize pollen in the method of the present invention.
Figure 7:
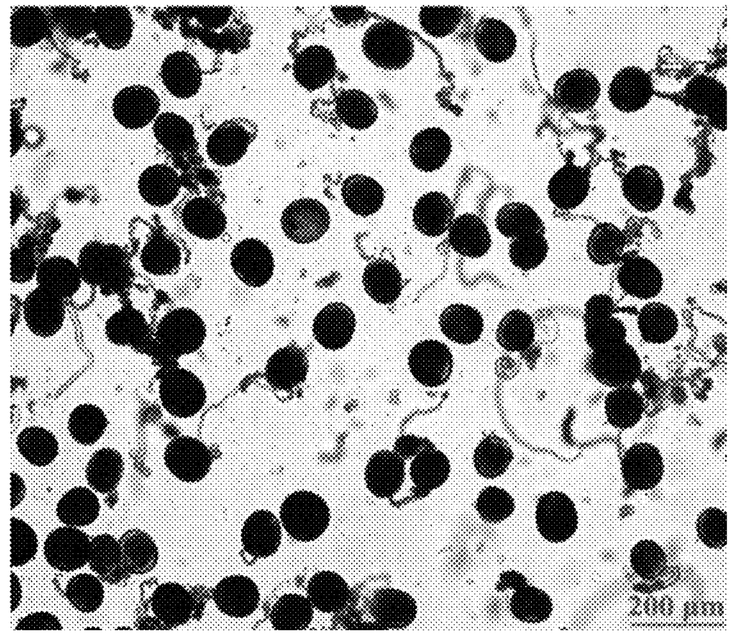
FIG. 7 shows germination of maize pollen after treatment at 4° C. for 30 minutes in the method of the present invention.
Figure 8:
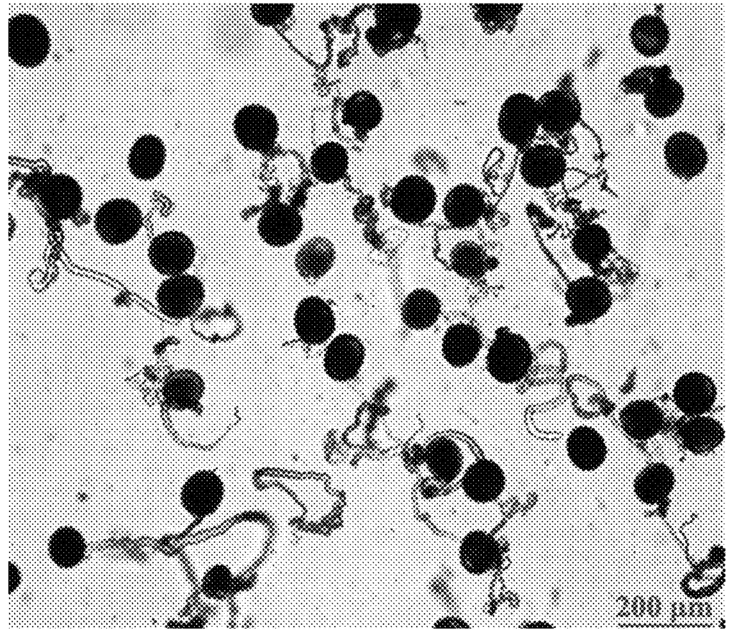
FIG. 8 shows germination of maize pollen after treatment at 8° C. for 30 minutes in the method of the present invention.
Figure 9:
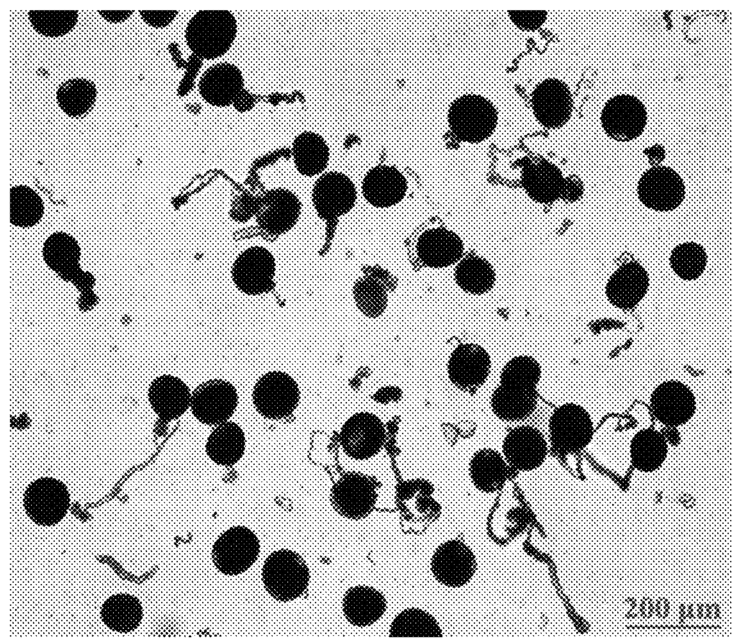
FIG. 9 shows germination of maize pollen after treatment at 12° C. for 30 minutes in the method of the present invention.
Figure 10:
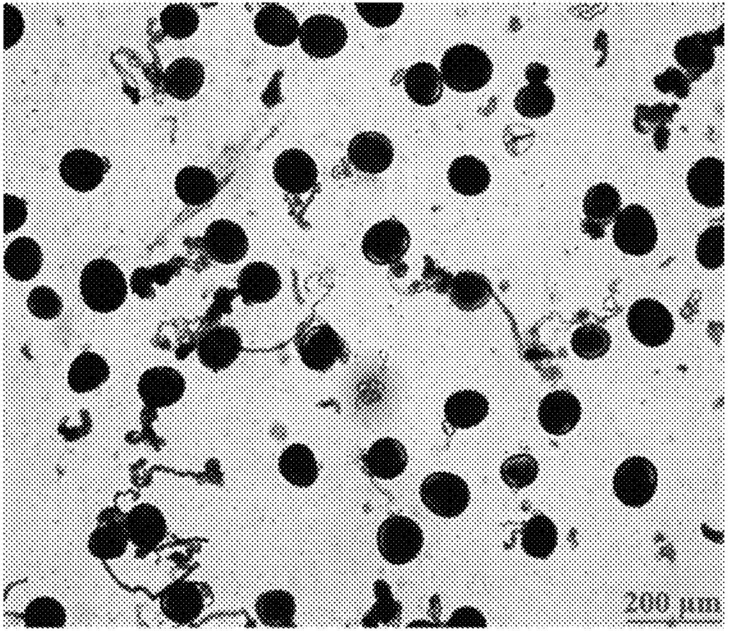
FIG. 10 shows germination of maize pollen after treatment at 16° C. for 30 minutes in the method of the present invention.
Figure 11:
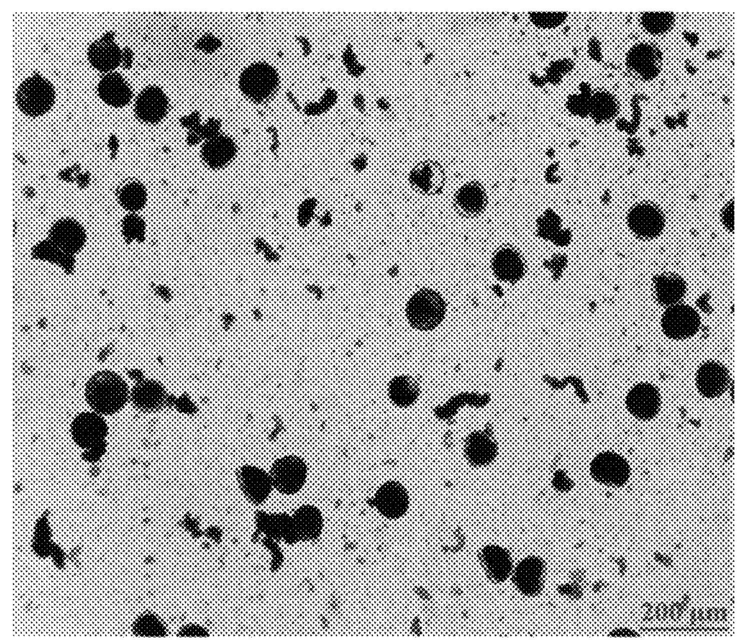
FIG. 11 shows germination of maize pollen after treatment at room temperature for 30 minutes in the method of the present invention.
Figure 12:
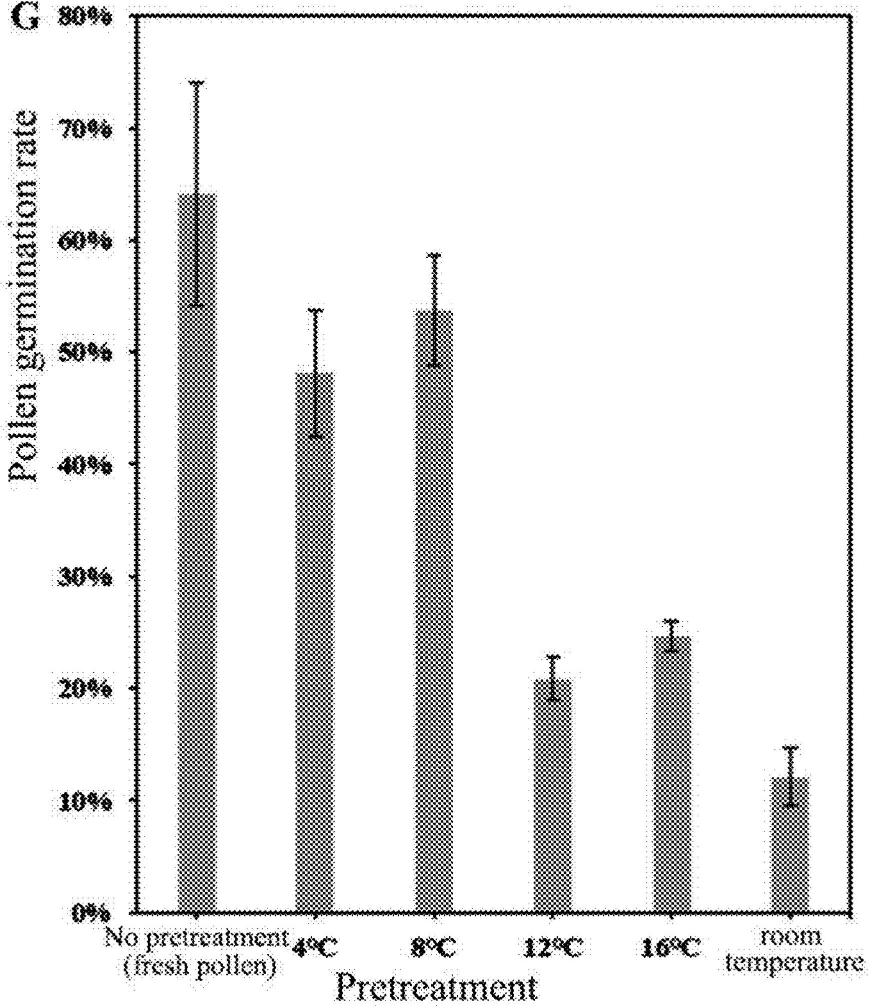
FIG. 12 shows statistics of the germination rate of maize pollen after 30 minutes of treatment in transfection solutions at different temperatures in the method of the present invention; the "No pretreatment (fresh pollen)" control was not subjected to the 30-minute transfection-solution pretreatment.
Figure 13:
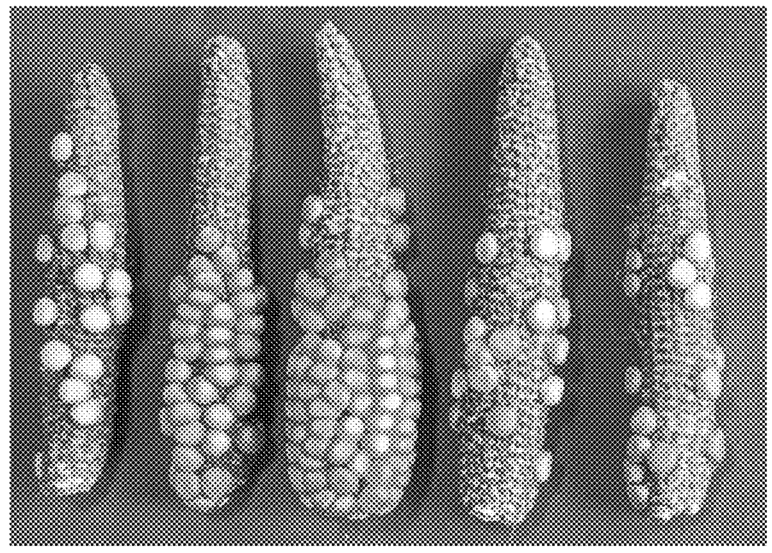
FIG. 13 shows maize setting of maize inbred line HZ178 magnetically transfected at low temperature (8° C.) in the method of the present invention.
Figure 14:
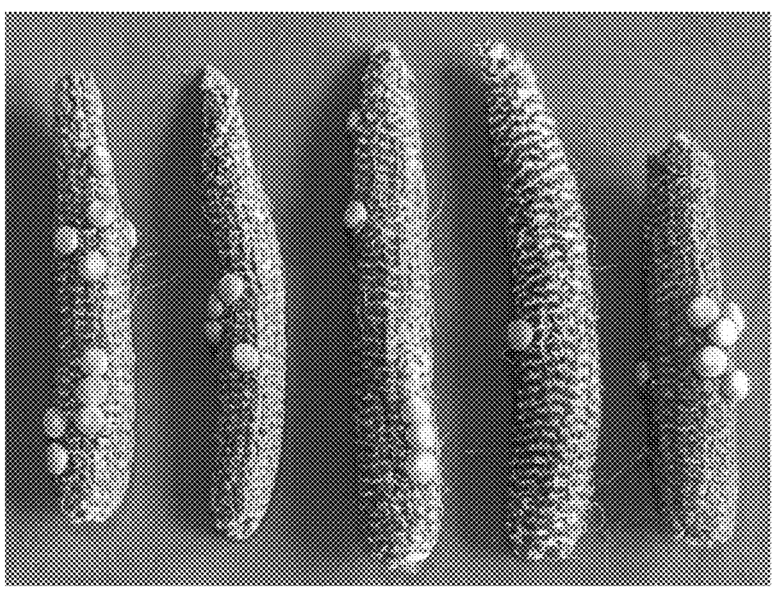
FIG. 14 shows maize setting of maize inbred line HZ178 magnetically transfected at room temperature in the method of the present invention.
Figure 15:
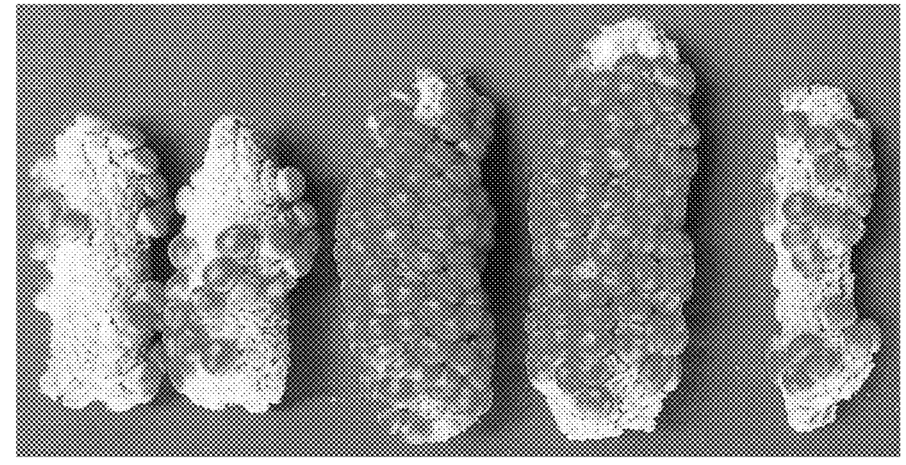
FIG. 15 shows maize setting of maize inbred line Jing 92 magnetically transfected at low temperature (8° C.) in the method of the present invention.
Figure 16:
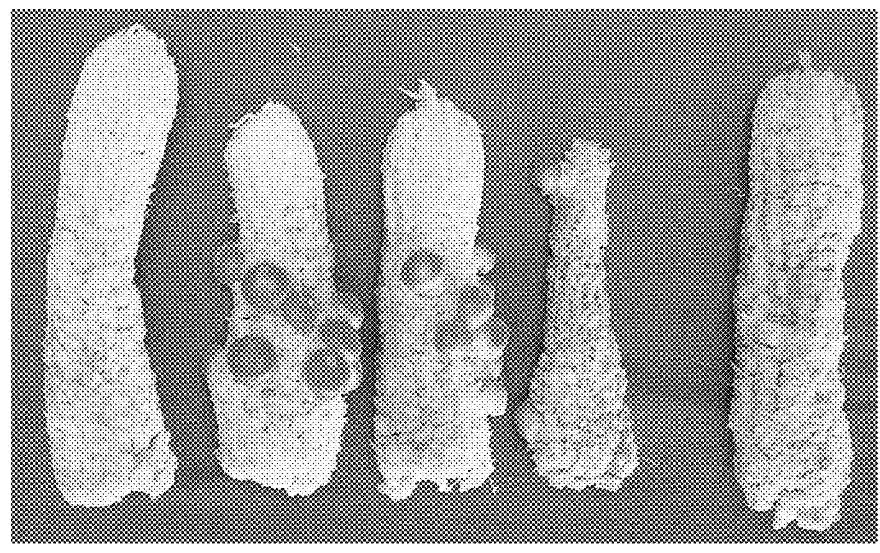
FIG. 16 shows maize setting of maize inbred line Jing 92 magnetically transfected at room temperature in the method of the present invention.

(6) After magnetic transfection, the pollen centrifuge tube was clamped in a pre-cooled ice bag at 8° C. and quickly taken to the field in an ice box; the pollen was gently shaken upside down and pollinated on 10 ears of maize inbred lines (pre-bagged) that were spitting; a drop of pollen suspension was added to the maize filaments truncated to approximately 2 cm long with a de-tipped 1 mL tip, 1 mL/ear, and the pollen suspension was spread evenly with gloves (FIG. 4). After pollinating the pollen of one plasmid, the pollen of the next plasmid was pollinated with a new glove. 20 days after the pollination, fruiting seeds were visible (FIG. 5).

Low Temperatures can Better Maintain Maize Pollen Viability.

1) Effect of transformation solution treatment and temperature on the viability of maize pollen.

Pollen viability was observed by germination of maize pollen in 15 mm diameter glass-bottomed dishes, with fresh maize pollen as control (-), without transformation-solution pretreatment. Approximately 5 mg of fresh maize pollen (-), without transformation-solution pretreatment, was added to 200 μL of pollen germination culture solution (15% PEG4000, 150 g/L sucrose, 300 mg/L $Ca(NO_3)_2 \cdot 4H_2O$, 100 mg/L $H_3BO_3$, 200 mg/L $MgSO_4 \cdot 7H_2O$, 100 mg/L $KNO_3$ and 0.1 mM $GA_3$); 20 μL of pollen suspension (pre-treated for 30 minutes at 4° C., 8° C., 12° C., 16° C. and room temperature in transformation solution, equivalent to $2\times10^4$ pollen grains) were also added in 180 μL of pollen germination culture solution; stirred gently and incubated for 3 hours at 25° C. in the dark before observing pollen germination under a microscope and taking photographs for counting. The results of pollen germination of the maize inbred line Jing 92 are shown in FIGS. 6 to 12. At 4° C., 8° C., 12° C., 16° C. and room temperature, the pollen germination rates for 30 minutes of pretreatment with the transformation solution were 48% (153/318), 54% (579/1077), 21% (130/623), 25% (136/552) and 12% (113/935) respectively. The pollen pretreated in the transformation solution for 30 minutes at 8° C. had the highest germination rate and maintained 75% of the viability of pollen pretreated without transformation solution (64%, 719/1121). A similar effect was observed in four maize varieties, Jing 92, HZ 178, Zheng 58 and 178, where pollen pretreated in transformation solution for 30 minutes at 8° C. had a higher germination rate than room temperature pretreatment (Table 1).

TABLE 1

Pollen germination rate of four maize inbred lines with/without transformation solution pretreatment at 8° C. and at room temperature

| Maize variety | Transformation liquid treatment for 30 minutes | Temperature | Total pollen count | Germinated pollen count | Germination rate (%) |
|---|---|---|---|---|---|
| Jing 92 | − | − | 1121 | 719 | 64.14 ± 9.97 |
| | + | 8° C. | 1077 | 579 | 53.76 ± 4.96 |
| | + | room temperature | 935 | 113 | 12.09 ± 2.62 |
| | − | − | 657 | 482 | 73.36 ± 8.62 |
| HZ178 | + | 8° C. | 701 | 280 | 39.94 ± 2.81 |
| | + | room temperature | 760 | 95 | 12.50 ± 2.38 |
| | − | − | 533 | 350 | 65.67 ± 11.78 |
| Zheng 58 | + | 8° C. | 693 | 381 | 54.98 ± 5.37 |
| | + | room temperature | 601 | 46 | 7.65 ± 2.50 |
| 178 | − | − | 785 | 473 | 60.25 ± 3.89 |
| | + | 8° C. | 548 | 174 | 31.75 ± 1.17 |

2) Higher fruit-setting in low temperature magnetically transfected maize. At the end of the magnetic transfection, the transfected pollen was pollinated to the ears of maize, and after the seeds had matured, they were harvested, photographed and the fruit-setting rate counted. The results are shown in FIGS. 13 to 16 and in the table below. Maize pollinated by magnetically transfected pollen at 8° C. had a fertility rate of 40 to 68 seeds/ear, which was significantly higher than that of maize pollinated by room temperature magnetically transfected pollen (9-10 seeds/ear), indicating that low temperature magnetic transfection was more conducive to maintaining pollen viability, improving fertility and obtaining more maize seeds for screening and identification.

| Maize variety | Magnetic transfection temperature | Number of ears harvested | Total seeds count | Ear average seed setting rate (seed/ear) |
|---|---|---|---|---|
| HZ178 | 8° C. | 5 | 199 | 39.8 |
| | room temperature | 5 | 51 | 10.2 |
| Jing 92 | 8° C. | 6 | 407 | 67.83 |
| | room temperature | 3 | 28 | 9.33 |

The aperture opening of maize pollen is essential for the introduction and expression of exogenous genes.

Figure 17:
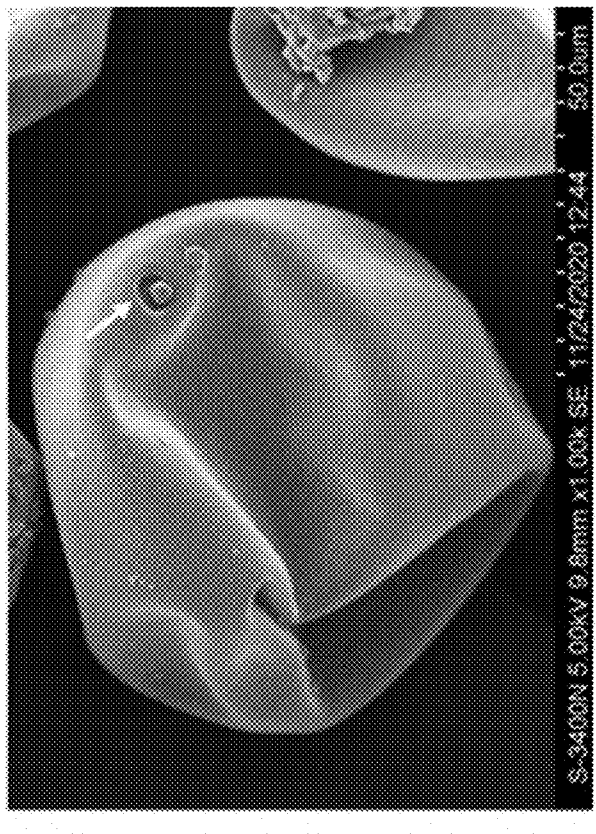
FIG. 17 shows maize pollen apertures at room temperature in the method of the present invention.
Figure 17:
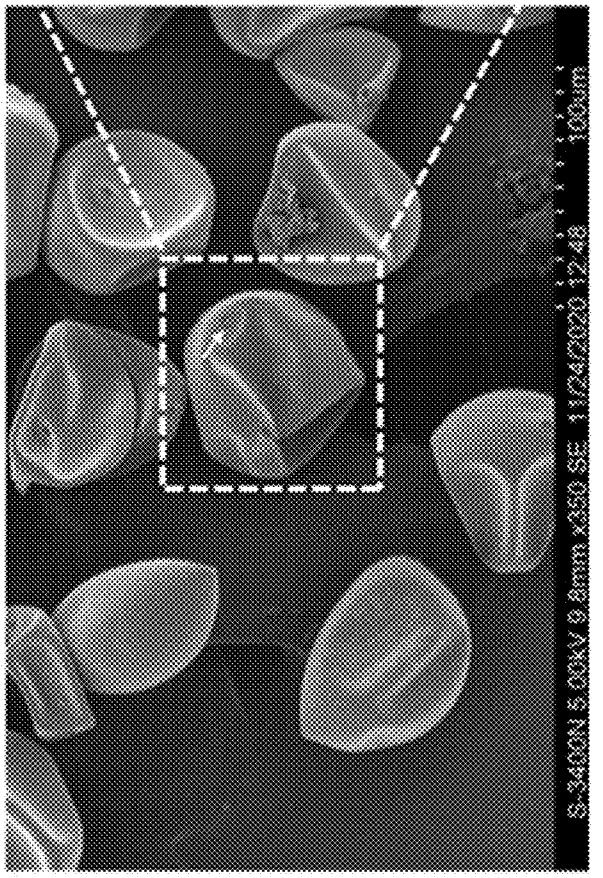
Figure 18:
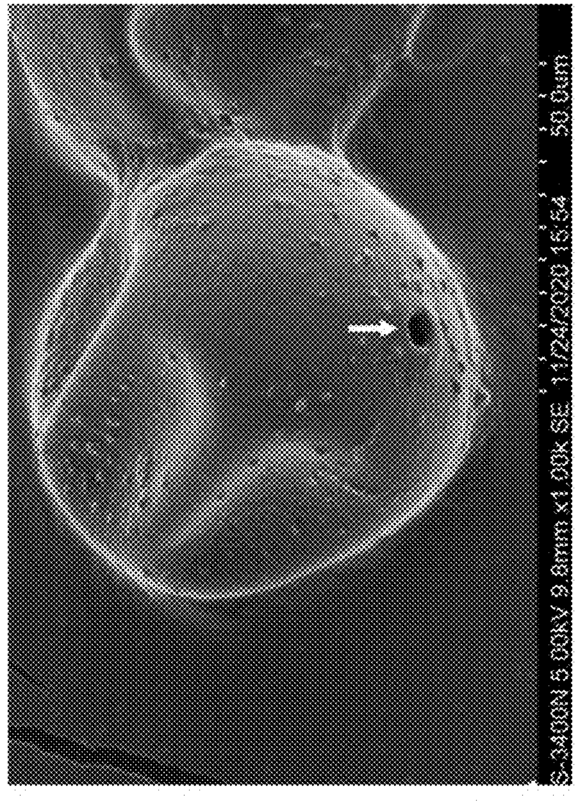
FIG. 18 shows that some maize pollen apertures after the operculum have been induced to open after pretreatment with transformation solution for 10 minutes at 8° C. in the method of the present invention.
Figure 18:
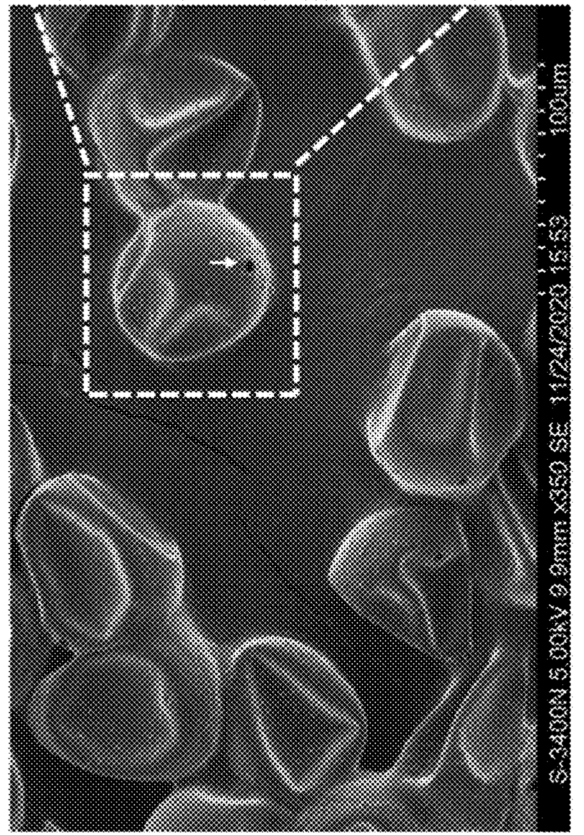

To investigate the effect of pollen apertures on DNA introduction into maize pollen, we first looked at the surface structure of maize pollen apertures under scanning electron microscopy. Maize pollen usually has only one pollen aperture with operculum (FIG. 17), which prevents the entry of external material. This is common in cereal pollen. Secondly, we studied the opening or otherwise of pollen apertures at 8° C. Pretreatment with transformation solution at 8° C. for 10 minutes induced the opening of the operculum of some maize pollen (FIG. 18), removing the barrier to entry of exogenous DNA into the pollen. Subsequently, we studied the pollen aperture opening rates of four maize inbred lines, Jing 92, HZ 178, Zheng 58 and 178, after treatment with transformation solution at room temperature or 8° C. for 10 minutes. As shown in the table below, pollen treated at 8° C. maintained an opening rate of 40-50%, which, although slightly lower than the room temperature treatment, was sufficient for magnetic transfection of maize pollen.

| Maize variety | Opening temperature | Total number of visible pollen apertures | Number of open aperture pollen (transformation solution treated for 10 minutes) | Opening rate (%) |
|---|---|---|---|---|
| Jing 92 | room temperature | 1276 | 695 | 54.47 ± 9.13 |
| | 8° C. | 9512 | 3838 | 40.35 ± 10.88 |
| HZ178 | room temperature | 7706 | 4748 | 61.61 ± 13.40 |
| | 8° C. | 11853 | 6044 | 50.99 ± 18.20 |
| Zheng 58 | room temperature | 4726 | 2496 | 52.81 ± 12.77 |
| | 8° C. | 6542 | 3224 | 49.28 ± 14.52 |
| 178 | 8° C. | 11068 | 4479 | 40.47 ± 4.39 |

Figures 19, 20:
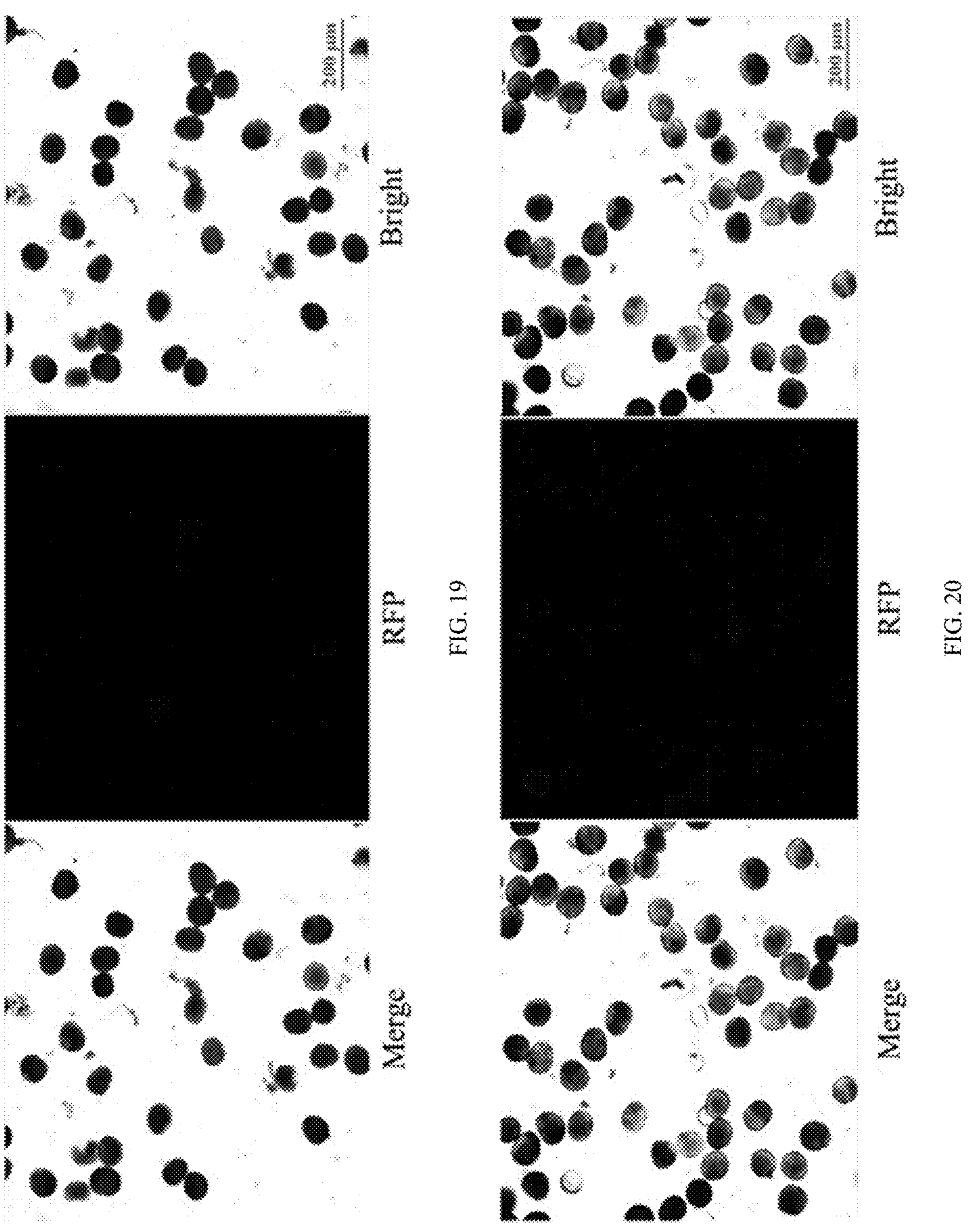
FIG. 19 shows fluorescence expression of pollen transfected with nanomagnetic beads (MNP) only by pretreatment with transformation solution for 10 minutes at 8° C., followed by magnetic transfection in the method of the present invention; RFP: red fluorescent field; Merge: red fluorescent field and bright field overlay image; Bright: bright field.
FIG. 20 shows fluorescence expression of pollen transfected with RFP plasmid DNA only by pretreatment with transformation solution for 10 minutes at 8° C., followed by magnetic transfection in the method of the present invention; RFP: red fluorescent field; Merge: red fluorescent field and bright field overlay image; Bright: bright field.
Figures 21, 22:
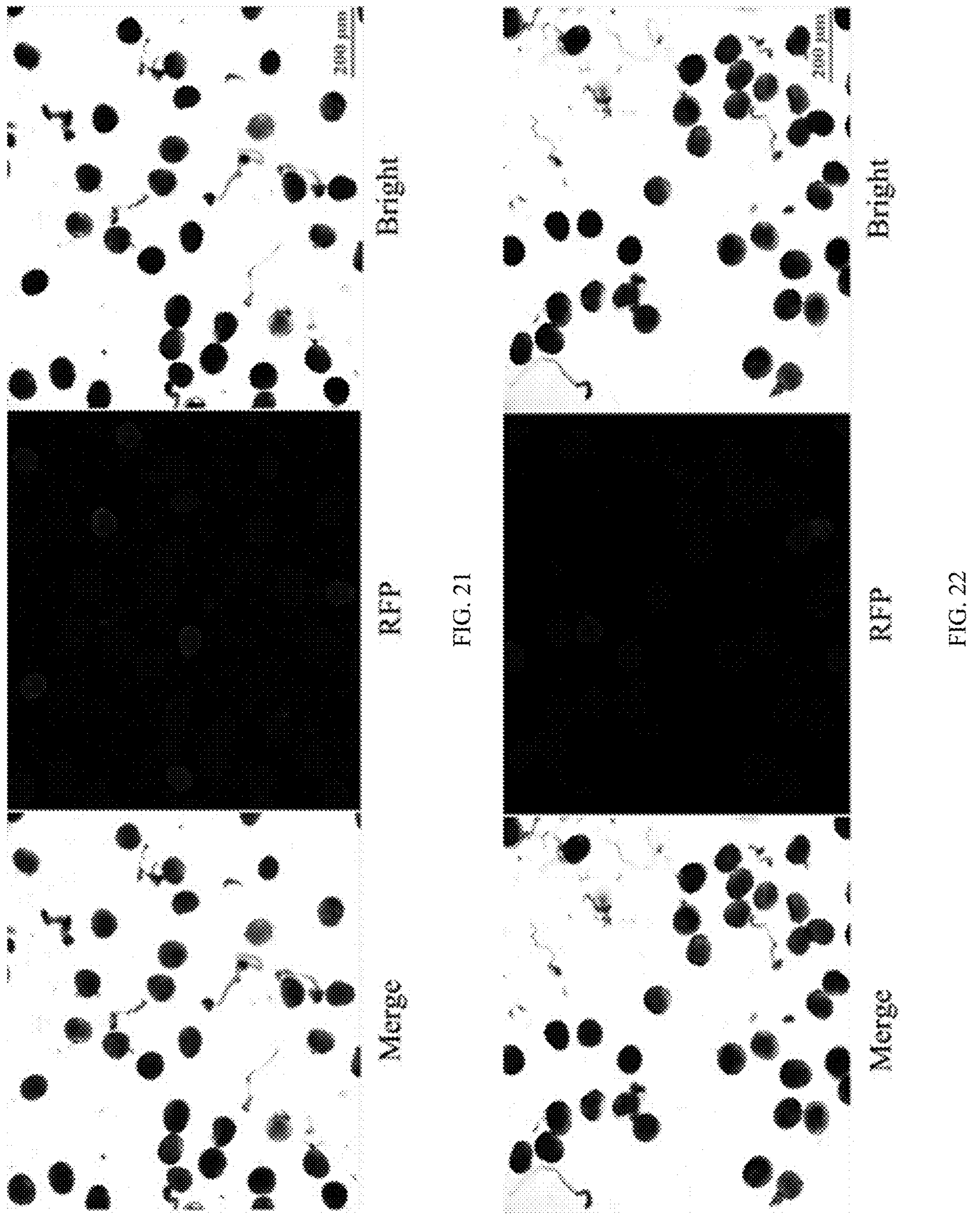
FIG. 21 shows fluorescence expression of pollen transfected with both MNP and RFP plasmid DNA by pretreatment with transformation solution for 10 minutes at 8° C., followed by magnetic transfection in the method of the present invention; RFP: red fluorescent field; Merge: red fluorescent field and bright field overlay image; Bright: bright field.
FIG. 22 shows fluorescence expression of maize pollen magnetically transfected with MNP and RFP plasmid DNA directly for 30 minutes at 8° C. without pretreatment with transformation solution for 10 minutes in the method of the present invention; RFP: red fluorescent field; Merge: red fluorescent field and bright field overlay image; Bright: bright field.
Figure 23:
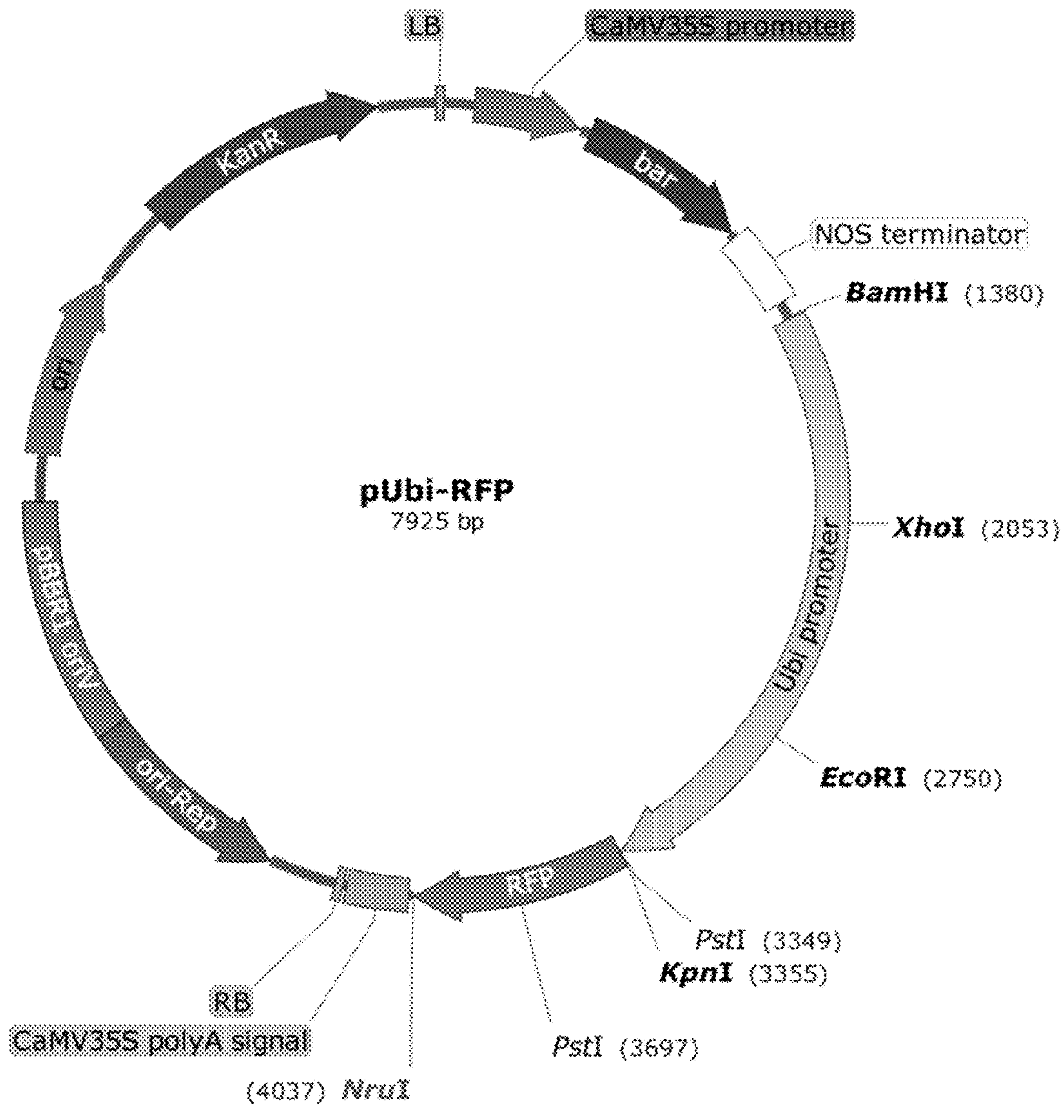
FIG. 23 shows a schematic diagram of the structure of the vector pUbi-RFP in the present invention.

We studied the transient expression of exogenous genes in maize pollen using red fluorescent protein (RFP) as a reporter gene (driven by the maize ubiquitin (Ubi) promoter, FIG. 23). After pretreatment with transformation solution for 10 min and magnetic field transfection for 20 min, maize pollen was transferred into the expression culture (20% PEG4000, 150 g/L sucrose, 300 mg/L $Ca(NO_3)_2 \cdot 4H_2O$, 100 mg/L $H_3BO_3$, 200 mg/L $MgSO_4 \cdot 7H_2O$, 100 mg/L $KNO_3$) and incubated at 25° C. for 20 h. Red fluorescence was not detected in pollen transfected with nanomagnetic beads (MNP) only (FIG. 19) or RFP plasmid DNA only (FIG. 20), but was detectable in 22% (129/590) of pollen transfected with both MNP and RFP plasmid DNA (FIG. 21). On the other hand, red fluorescence was detected in approximately 3% (6/208) of maize pollen that had been magnetically transfected with MNP and RFP plasmid DNA directly for 30 min at 8° C. without pretreatment with transformation solution for 10 min (FIG. 22). These results suggest that pretreatment with the transformation solution for 10 min was more effective in inducing pollen opening for exogenous gene entry and transient expression compared to direct transfection.

The herbicide screening marker gene bar can be efficiently introduced into the maize genome and stably inherited by magnetic pollen transfection.

Figure 24:
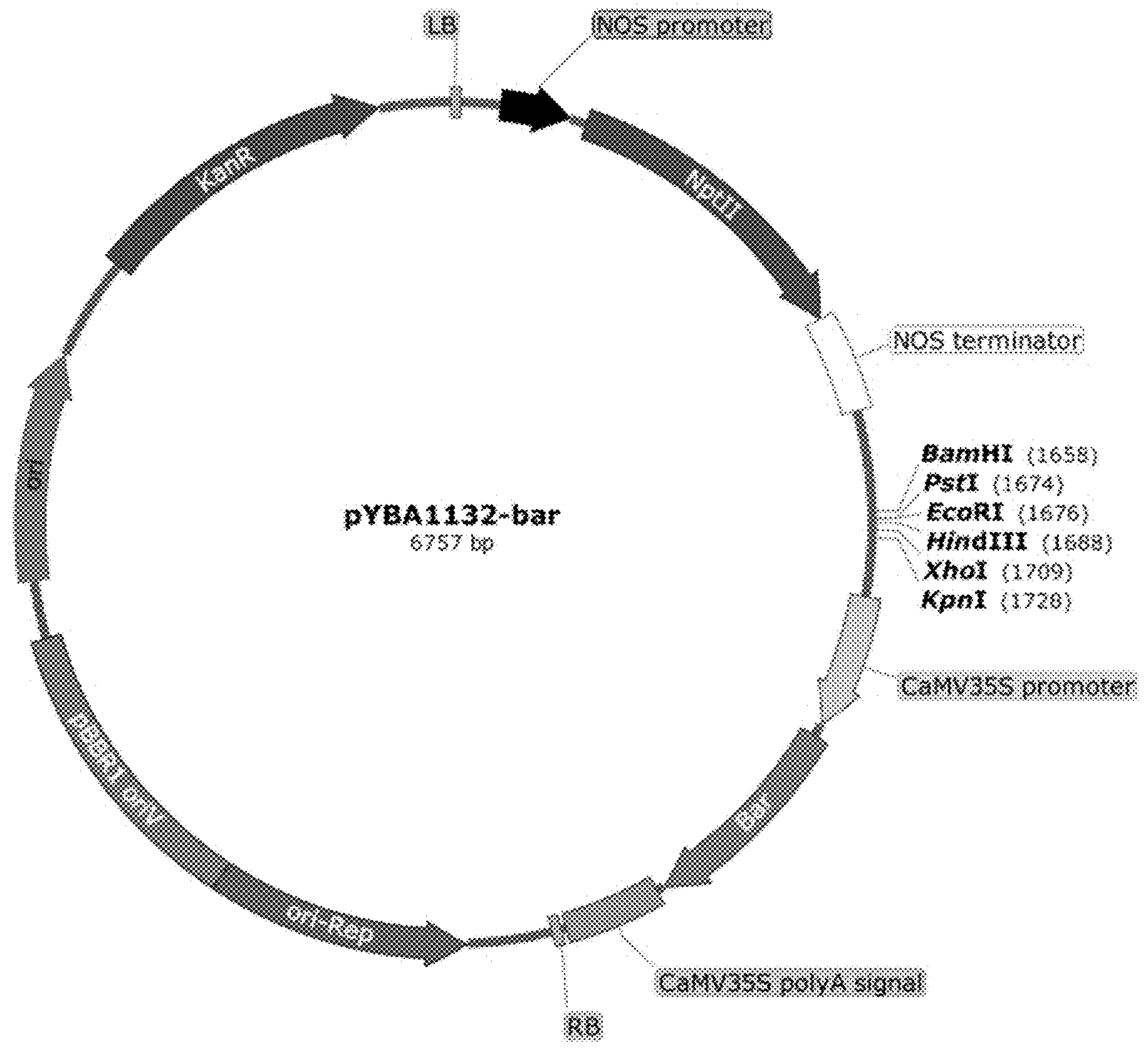
FIG. 24 shows a schematic diagram of the structure of the vector pYBA1132-bar in the present invention.
Figure 25:
FIG. 25 shows performance of T1 generation seedlings obtained by introduction into the maize inbred line Zheng 58 by means of magnetic pollen transfection in the present invention.
Figure 26:
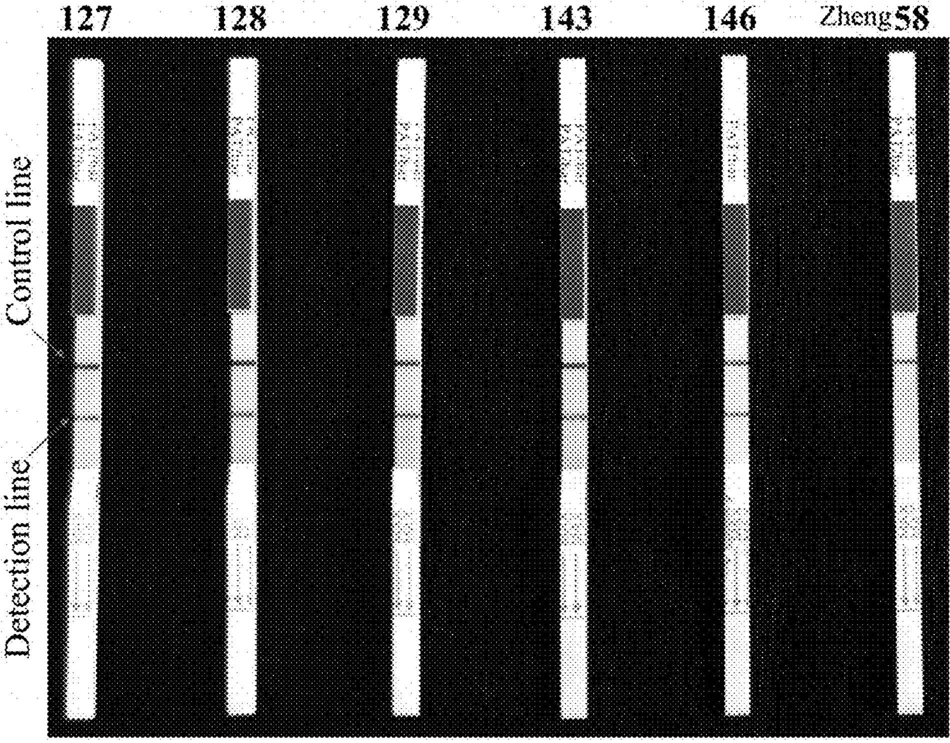
FIG. 26 shows the results of five glufosinate-resistant transgenic maize plants tested by bar/PAT rapid transgenic test strips in the present invention.
Figure 27:
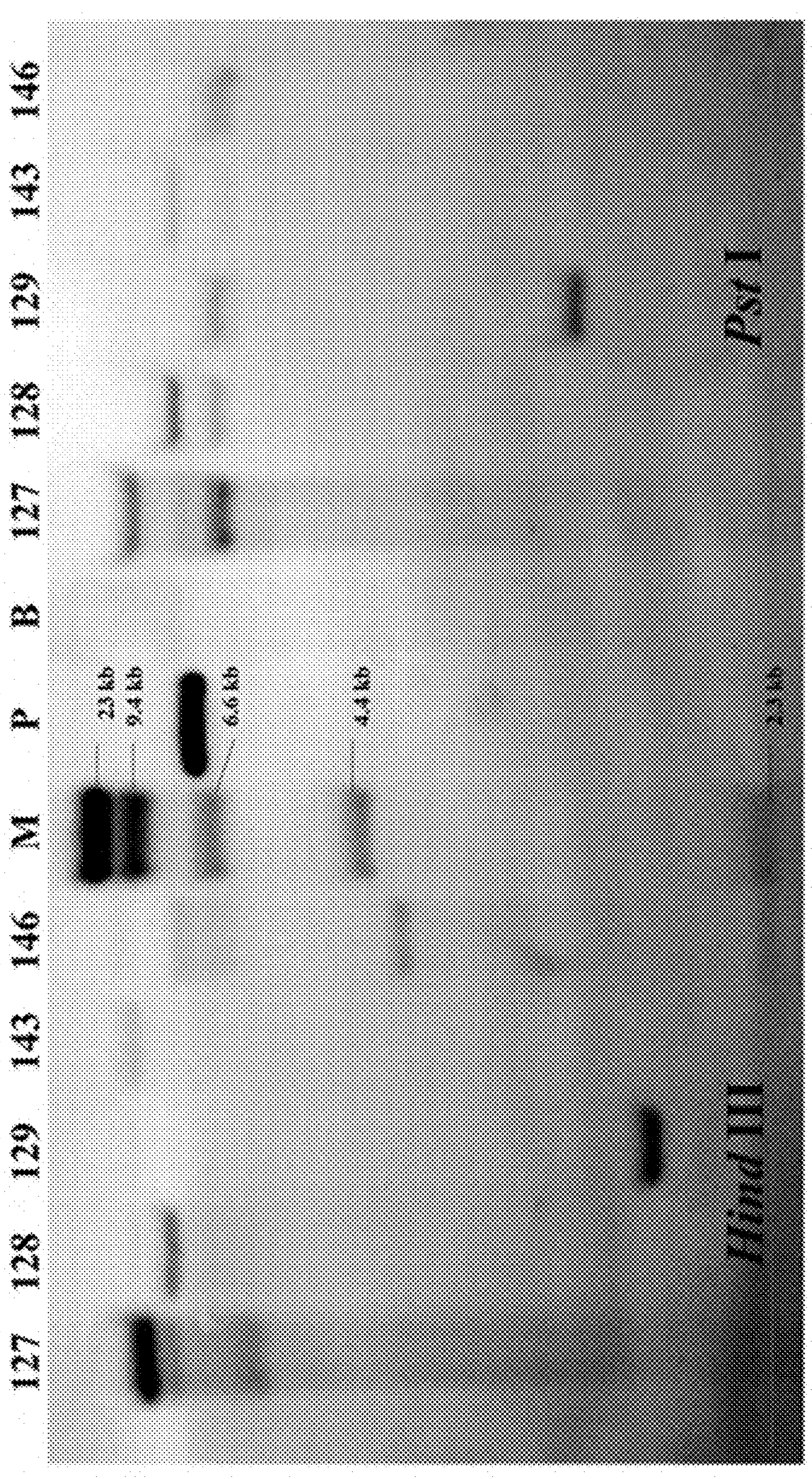
FIG. 27 shows the results of Southern hybridization of T1 generation maize plants in the present invention.
Figure 28:
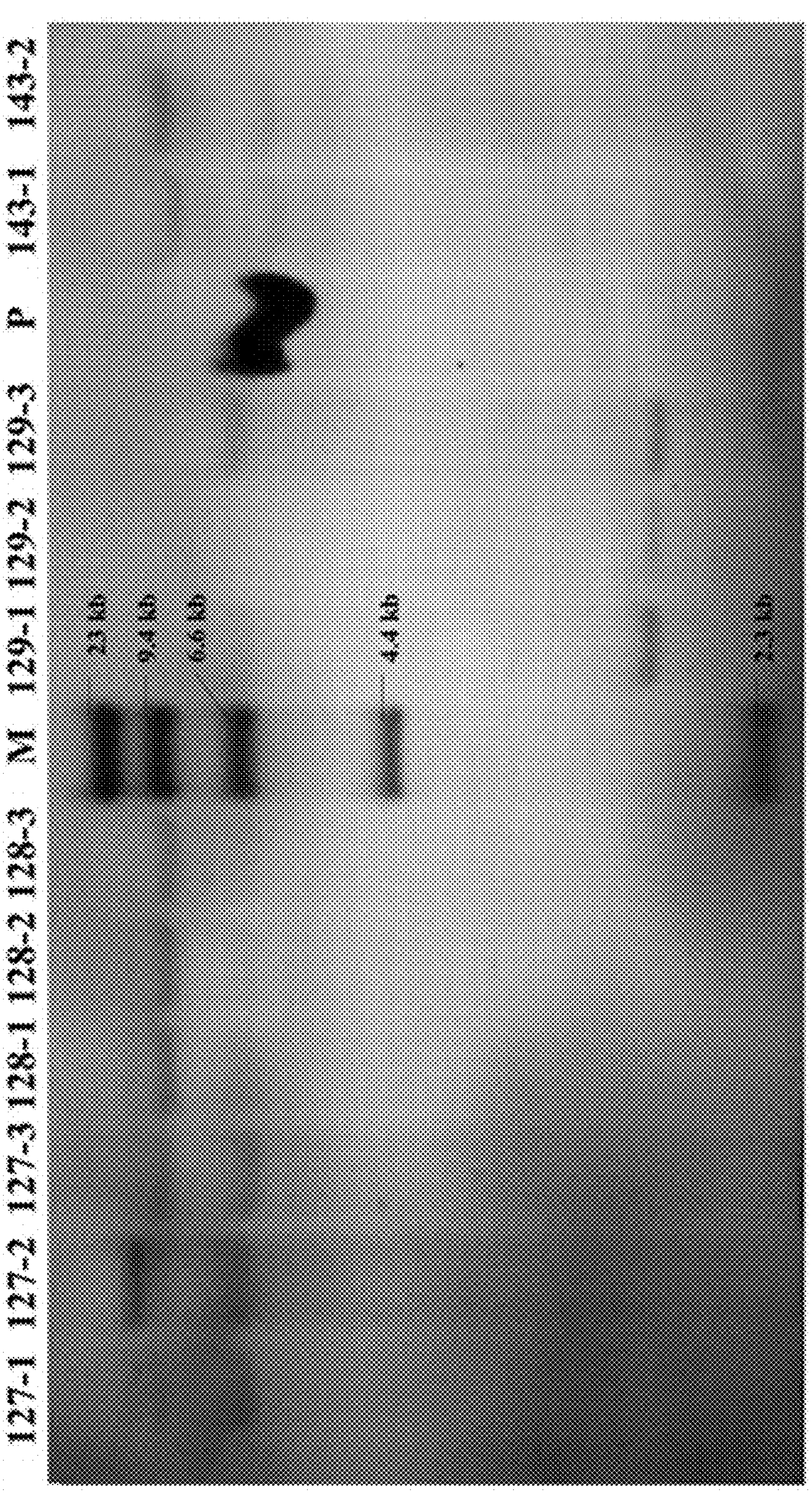
FIG. 28 shows the results of Southern hybridization of T2 generation maize plants in the present invention.

To screen stable transformed progeny, we introduced the herbicide selection marker gene bar (vector shown in FIG. 24) into the maize inbred line Zheng 58 by magnetic transfection of pollen. After screening at the three-leaf stage with 200 mg/L glufosinate, 1.41% (5/355) of the T1 generation seedlings showed herbicide resistance (FIG. 25). These five glufosinate resistant transgenic maize plants tested positive (with both detection and control lines) by the bar/PAT rapid transgenic test strip (FIG. 26), indicating that the bar gene was successfully introduced into maize by magnetic transfection of pollen and expressed normally. In addition, Southern hybridization results showed that these T1 generation maize plants had about 2-5 copies integrated in their genomes (FIG. 27) and all five transgenic lines inherited the bar gene to the T2 generation, where Southern hybridization testing revealed genetic segregation in the T2 generation (FIG. 28). The above findings show that by our magnetic transfection of maize pollen, exogenous genes were efficiently integrated into the maize genome and are normally expressed and stably inherited in the progeny.

Existing methods of transfecting maize pollen are carried out at room temperature, but maize pollen is highly susceptible to germination, inactivation and rupture at room temperature. We found that the room temperature magnetically transfected maize pollen maintained only about 10% viability and the pollinated maize ears had a fertility rate of only 10 seeds/ear. In contrast, maize pollen can be about 75% viable after magnetic transfection at a low temperature of 8° C., and its pollinated female maize ears could have an increased fertility of up to 60 seeds/ear. In this way, low-temperature magnetic transfection of maize pollen can dramatically increase fertility and yield more transformed seeds for subsequent screening and identification. In addition, existing maize pollen transfection methods are not pre-treated for aperture opening. Because the pollen apertures of maize are usually capped, when direct magnetic transfection is performed, the efficiency of nanomagnetic beads to introduce exogenous DNA into pollen is only 2%. However, at a low temperature of 8° C., which can maintain the viability of maize pollen, 40 to 50% of the maize pollen aperture operculum will be opened after pretreatment with transformation solution for 10 minutes, at which point the efficiency of the nanomagnetic beads to introduce exogenous DNA into pollen could be increased to 22%. Based on the above two aspects, the improved maize pollen magnetic transfection method in this application can not only maintain the vitality of most of the maize pollen through low temperature environment, but also improve the efficiency of exogenous DNA introduction through aperture opening pretreatment, and has a wide application prospect.

The foregoing embodiments are merely illustrative of preferred embodiments of the present invention and are not intended to limit the scope of the present invention. Various variations and modifications made to the technical solutions of the present invention by those skilled in the art without departing from the spirit of the present invention are embraced in the protection scope of the present invention as defined by the appended claims.

What is claimed is:

1. A method for magnetic transfection of maize pollen, consisting of the following steps:

(1) preparing plasmid DNA for transfection;

(2) binding magnetic nanoparticles (MNP) nanomagnetic beads to the plasmid DNA at room temperature to form an MNP-DNA complex;

(3) collecting fresh pollen from maize at full flowering and transporting the collected pollen to a laboratory in an insulated icebox isolated from meltwater;

(4) mixing sieved maize pollen with a maize pollen transformation solution pre-cooled at 8° C. to obtain a pollen mixture, wherein the maize pollen transformation solution comprises sucrose 0.5 mol/L, $H_3BO_3$ 1 mmol/L, $KNO_3$ 1 mmol/L, $Ca(NO_3)_2 \cdot 4H_2O$ 1 mmol/L, $MnSO_4 \cdot H_2O$ 1 mmol/L, $MgSO_4 \cdot 7H_2O$ 1 mmol/L, and $GA_3$ 0.1 mmol/L; and subjecting the pollen mixture to an aperture-opening pre-treatment at 8° C. for 10 min prior to adding the MNP-DNA complex;

(5) after completion of the aperture-opening pre-treatment of step (4), adding the MNP-DNA complex obtained in step (2) to the pollen mixture, mixing and placing the pollen mixture on a magnetic plate pre-cooled at 8° C. for transfection at 8° C. for a total of 20 min; and (6) after transfection, taking the pollen suspension to a maize field in an ice box and pollinating directly on ears of maize.

2. The method for magnetic transfection of maize pollen according to claim 1, wherein step (1) comprises:

extracting plasmid DNA for transfection;

adjusting the extracted plasmid DNA to a concentration of 1000±50 ng/μL with $ddH_2O$;

dispensing the adjusted plasmid DNA in microcentrifuge tubes and storing the dispensed plasmid DNA frozen at −20° C. to avoid repeated freeze-thawing; and prior to magnetic transfection, thawing the plasmid DNA to room temperature.

3. The method of claim 2, wherein step (2) comprises:

based on the flowering status of maize inbred lines and plasmid transformation requirement, estimating the transformation trials to be carried out on the day;

allowing the MNP nanomagnetic beads to stand at room temperature for 10 min; and providing a 200 μL PCR tube, adding and mixing by aspiration 160 μL of $ddH_2O$, 7.5 μL of 1 μg/μL of the MNP nanomagnetic beads and 30 μL of 1 μg/μL of the plasmid DNA in the PCR tube, and allowing the PCR tube to stand at room temperature for 20 min or more to obtain the MNP-DNA complex.

4. The method of claim 3, wherein step (3) comprises:

collecting fresh pollen in paper bags from maize inbred lines at flowering; and placing the paper bags with the fresh pollen collected therein in plastic self-sealing bags, sandwiching the plastic self-sealing bags between ice packs, and bringing the plastic self-sealing bags back to a chamber in ice boxes for magnetic transfection.

5. The method of claim 4, wherein step (4) comprises:

removing anthers from the fresh pollen obtained in step (3) using a 100 mesh sieve to obtain the sieved maize pollen;

weighing 2 g of the sieved maize pollen and transferring the 2 g of the sieved maize pollen to a 15 mL round-bottom centrifuge tube;

adding 8 mL of the maize pollen transformation solution of claim 1 pre-cooled at 8° C. in the centrifuge tube; and inverting and mixing the sieved maize pollen and the maize pollen transformation solution in the centrifuge tube, and placing the centrifuge tube horizontally for aperture-opening for 10 min in an 8° C. incubator.

6. The method of claim 5, wherein step (5) comprises:

adding the MNP-DNA complex obtained in step (2) entirely to the aperture-opening pre-treatment mixture in step (4) to a total volume of 10 mL;

inverting and mixing the MNP-DNA complex and the aperture-opening pre-treatment mixture;

placing the centrifuge tube on a MagnetoFACTOR-96 plate pre-cooled in an incubator at 8° C., and placing the centrifuge tube on the MagnetoFACTOR-96 plate horizontally for transfection for 10 min;

inverting and mixing the MNP-DNA complex and the aperture-opening pre-treatment mixture once again; and placing the centrifuge tube on the MagnetoFACTOR-96 plate horizontally for transfection for another 10 min.

* * * * *